(12) United States Patent
Nakamura

(10) Patent No.: US 6,699,837 B2
(45) Date of Patent: *Mar. 2, 2004

(54) TREATMENT OF NEURONS WITH HGF

(76) Inventor: Toshikazu Nakamura, 10-27, Takamidai, Takatsuki-shi, Osaka 569 (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/605,221
(22) PCT Filed: Sep. 16, 1994
(86) PCT No.: PCT/JP94/01533
§ 371 (c)(1),
(2), (4) Date: Mar. 15, 1996
(87) PCT Pub. No.: WO95/07709
PCT Pub. Date: Mar. 23, 1995

(65) Prior Publication Data
US 2003/0060403 A1 Mar. 27, 2003

(30) Foreign Application Priority Data
Sep. 17, 1993 (JP) ............................................. 5-254859

(51) Int. Cl.[7] .............................................. A61K 38/18
(52) U.S. Cl. ........................................... 514/12; 514/2
(58) Field of Search ....................... 514/2, 12; 530/399

(56) References Cited

U.S. PATENT DOCUMENTS 5,227,158 A * 7/1993 Jardieu ...................... 424/85.5

OTHER PUBLICATIONS

The Merck Manual of Diagnosis and Therapy (1992), 16th edition, ed. Robert Berkow, Merck Research Laboratories, Rathway, NJ, pp. 1450–1457.*
Nakamura et al. Nature 342 (1989) 440–443.*
Lieberman, International Rev of Neurobiol. 14(1971) 49–124.*
Jackowski, British J. of Neurosurgery 9(1995) 303–317.*
Rudinger, In "Peptide Hormones", (Jun. 1976), ed. J.A. Parsons, University Park Press, Baltimore, pp. 1–7.*
Di Renzo et al., Oncogene, vol. 8 (1993) pp. 219–222.
Di Renzo et al., Oncogene, vol. 6 (1991) pp. 1997–2003.
Sonnenberg et al., J. Cell Bio., vol. 123, No. 1 (1993) pp. 223–235.
Sun et al., *Society for Neuroscience*, vol. 25, No. 301.9, (1999), p. 765.
Wheeler et al., *Society for Neuroscience*, vol. 25, No. 301.19, (1999), p. 766.
Zhang et al., *Society for Neuroscience*, vol. 25, No. 706.15, (1999), p. 1781.
Yang et al., *The Journal of Neuroscience*, vol. 18, No. 20, (Oct. 15, 1998), pp. 8369–8381.
Hamanoue et al., *Journal of Neuroscience Research*, vol. 43, (1996), pp. 554–564.
Yamagata et al., *Biochemical and Biophysical Research Communications*, vol. 210, No. 1, (1995), pp. 231–237.
Maina et al., *Neuron*, vol. 20, (May 1998), pp. 835–846.

* cited by examiner

*Primary Examiner*—Gary Kunz
*Assistant Examiner*—Robert C. Hayes
(74) *Attorney, Agent, or Firm*—Birch, Stewart, Kolasch & Birch, LLP

(57) ABSTRACT

The invention relates to a therapeutic agent for disorder in brain and nerve containing HGF (hepatocyte growth factor) as an active ingredient, and a method for treatment of disorder in brain and nerve comprising administration of HGF. The active ingredient HGF possesses an action to prolong survival of brain and nerve cells, and the injured brain or nerves may be regenerated and restored. Therefore, the therapeutic agent and method for treatment of the invention are useful for prevention and treatment of various disorder in brain and nerve (for example, dementia, senile dementia of Alzheimer type, cerebral stroke, and cerebral infarction).

3 Claims, 8 Drawing Sheets

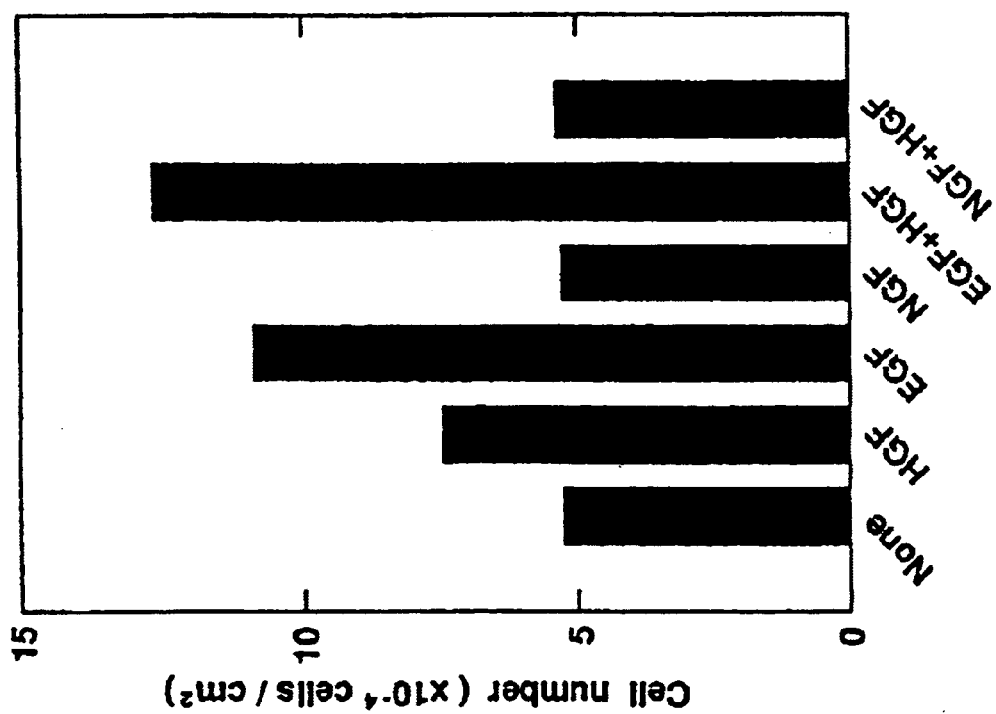
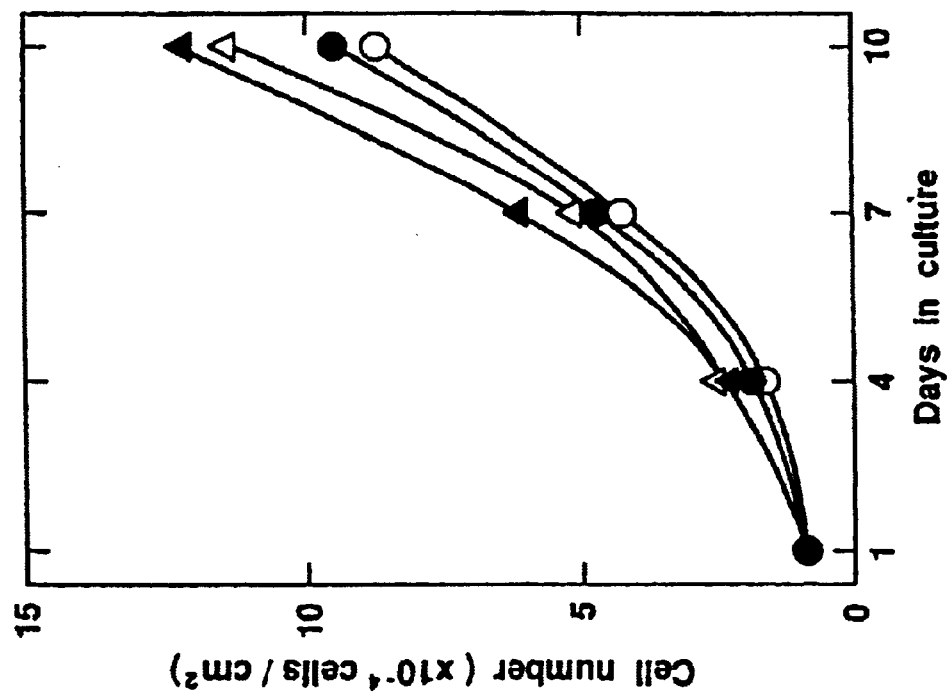

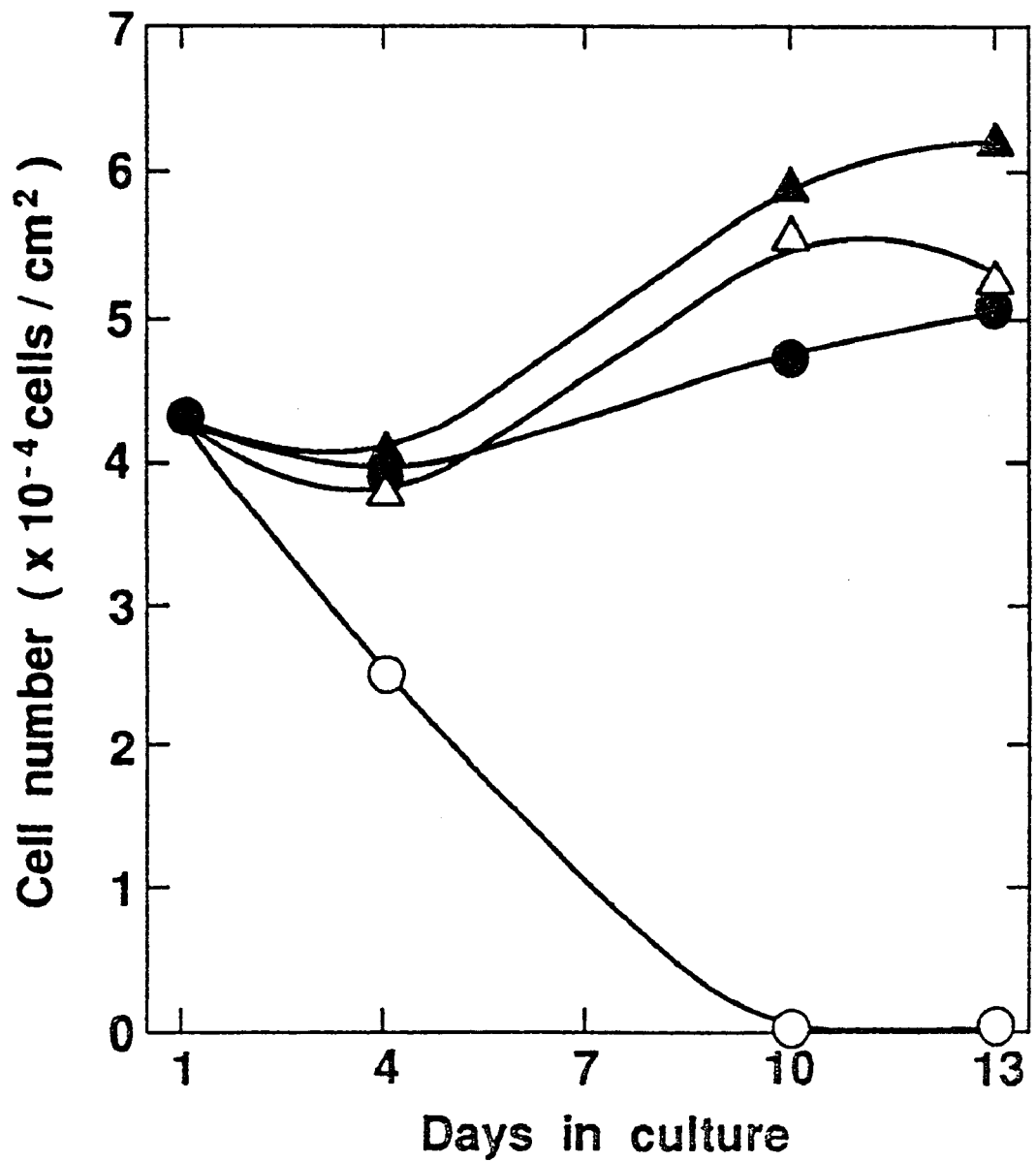

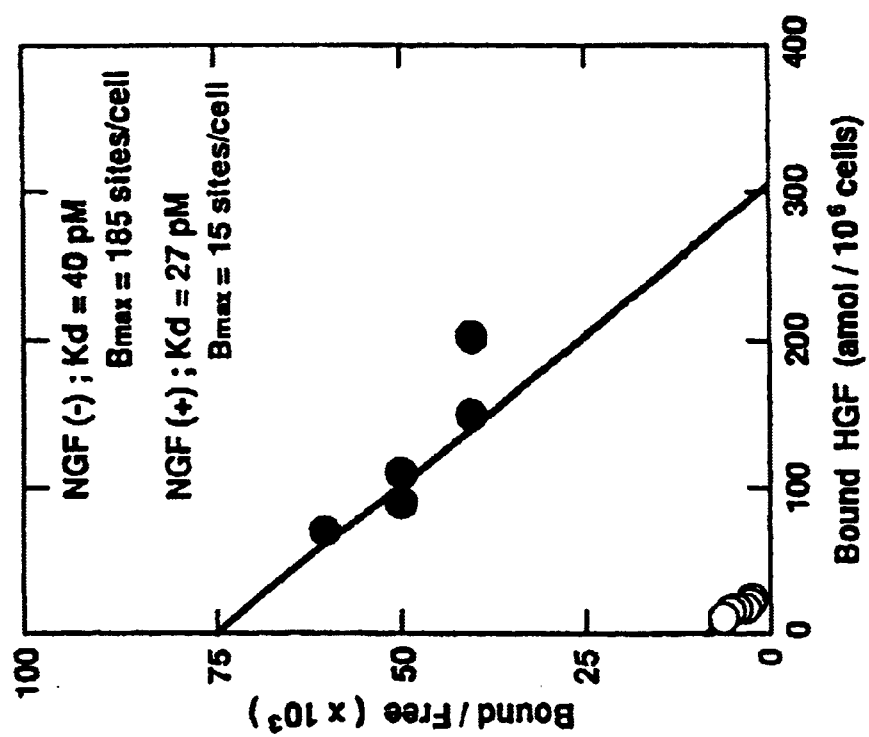
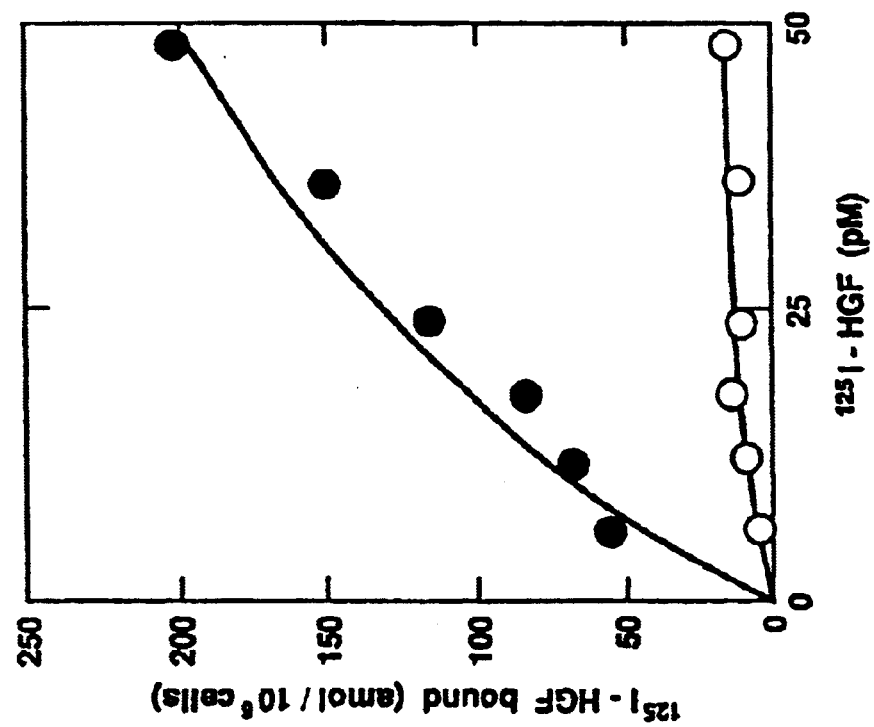
Fig. 6(A)
Fig. 6(B)

1 day in culture

┌ 6 days in culture ┐

None        HGF

SEQUENCE LISTING

```
<160> NUMBER OF SEQ ID NOS:  4

<210> SEQ ID NO 1
<211> LENGTH: 2214
<212> TYPE: DNA
<213> ORGANISM: Homo sapiens
<220> FEATURE:
<221> NAME/KEY: CDS
<222> LOCATION: (28)..(2211)
<223> OTHER INFORMATION: HGF-A (Full length HGF)

<400> SEQUENCE: 1
ggatccgcca gcccgtccag cagcacc atg tgg gtg acc aaa ctc ctg cca gcc      54
                                Met Trp Val Thr Lys Leu Leu Pro Ala
                                  1               5 ctg ctg ctg cag cat gtc ctc ctg cat ctc ctc ctg ctc ccc atc gcc      102
Leu Leu Leu Gln His Val Leu Leu His Leu Leu Leu Leu Pro Ile Ala
 10              15                  20                  25 atc ccc tat gca gag gga caa agg aaa aga aga aat aca att cat gaa      150
Ile Pro Tyr Ala Glu Gly Gln Arg Lys Arg Arg Asn Thr Ile His Glu
                30                  35                  40 ttc aaa aaa tca gca aag act acc cta atc aaa ata gat cca gca ctg      198
Phe Lys Lys Ser Ala Lys Thr Thr Leu Ile Lys Ile Asp Pro Ala Leu
            45                  50                  55 aag ata aaa acc aaa aaa gtg aat act gca gac caa tgt gct aat aga      246
Lys Ile Lys Thr Lys Lys Val Asn Thr Ala Asp Gln Cys Ala Asn Arg
        60                  65                  70 tgt act agg aat aaa gga ctt cca ttc act tgc aag gct ttt gtt ttt      294
Cys Thr Arg Asn Lys Gly Leu Pro Phe Thr Cys Lys Ala Phe Val Phe
    75                  80                  85 gat aaa gca aga aaa caa tgc ctc tgg ttc ccc ttc aat agc atg tca      342
Asp Lys Ala Arg Lys Gln Cys Leu Trp Phe Pro Phe Asn Ser Met Ser
 90                  95                  100                 105 agt gga gtg aaa aaa gaa ttt ggc cat gaa ttt gac ctc tat gaa aac      390
Ser Gly Val Lys Lys Glu Phe Gly His Glu Phe Asp Leu Tyr Glu Asn
                110                 115                 120 aaa gac tac att aga aac tgc atc att ggt aaa gga cgc agc tac aag      438
Lys Asp Tyr Ile Arg Asn Cys Ile Ile Gly Lys Gly Arg Ser Tyr Lys
```

-continued

```
                125                 130                 135
gga aca gta tct atc act aag agt ggc atc aaa tgt cag ccc tgg agt    486
Gly Thr Val Ser Ile Thr Lys Ser Gly Ile Lys Cys Gln Pro Trp Ser
        140                 145                 150 tcc atg ata cca cac gaa cac agc ttt ttg cct tcg agc tat cgg ggt    534
Ser Met Ile Pro His Glu His Ser Phe Leu Pro Ser Ser Tyr Arg Gly
155                 160                 165 aaa gac cta cag gaa aac tac tgt cga aat cct cga ggg gaa gaa ggg    582
Lys Asp Leu Gln Glu Asn Tyr Cys Arg Asn Pro Arg Gly Glu Glu Gly
170                 175                 180                 185 gga ccc tgg tgt ttc aca agc aat cca gag gta cgc tac gaa gtc tgt    630
Gly Pro Trp Cys Phe Thr Ser Asn Pro Glu Val Arg Tyr Glu Val Cys
                190                 195                 200 gac att cct cag tgt tca gaa gtt gaa tgc atg acc tgc aat ggg gag    678
Asp Ile Pro Gln Cys Ser Glu Val Glu Cys Met Thr Cys Asn Gly Glu
                205                 210                 215 agt tat cga ggt ctc atg gat cat aca gaa tca ggc aag att tgt cag    726
Ser Tyr Arg Gly Leu Met Asp His Thr Glu Ser Gly Lys Ile Cys Gln
        220                 225                 230 cgc tgg gat cat cag aca cca cac cgg cac aaa ttc ttg cct gaa aga    774
Arg Trp Asp His Gln Thr Pro His Arg His Lys Phe Leu Pro Glu Arg
235                 240                 245 tat ccc gac aag ggc ttt gat gat aat tat tgc cgc aat ccc gat ggc    822
Tyr Pro Asp Lys Gly Phe Asp Asp Asn Tyr Cys Arg Asn Pro Asp Gly
250                 255                 260                 265 cag ccg agg cca tgg tgc tat act ctt gac cct cac acc cgc tgg gag    870
Gln Pro Arg Pro Trp Cys Tyr Thr Leu Asp Pro His Thr Arg Trp Glu
                270                 275                 280 tac tgt gca att aaa aca tgc gct gac aat act atg aat gac act gat    918
Tyr Cys Ala Ile Lys Thr Cys Ala Asp Asn Thr Met Asn Asp Thr Asp
                285                 290                 295 gtt cct ttg gaa aca act gaa tgc atc caa ggt caa gga gaa ggc tac    966
Val Pro Leu Glu Thr Thr Glu Cys Ile Gln Gly Gln Gly Glu Gly Tyr
        300                 305                 310 agg ggc act gtc aat acc att tgg aat gga att cca tgt cag cgt tgg    1014
Arg Gly Thr Val Asn Thr Ile Trp Asn Gly Ile Pro Cys Gln Arg Trp
315                 320                 325 gat tct cag tat cct cac gag cat gac atg act cct gaa aat ttc aag    1062
Asp Ser Gln Tyr Pro His Glu His Asp Met Thr Pro Glu Asn Phe Lys
330                 335                 340                 345 tgc aag gac cta cga gaa aat tac tgc cga aat cca gat ggg tct gaa    1110
Cys Lys Asp Leu Arg Glu Asn Tyr Cys Arg Asn Pro Asp Gly Ser Glu
                350                 355                 360 tca ccc tgg tgt ttt acc act gat cca aac atc cga gtt ggc tac tgc    1158
Ser Pro Trp Cys Phe Thr Thr Asp Pro Asn Ile Arg Val Gly Tyr Cys
                365                 370                 375 tcc caa att cca aac tgt gat atg tca cat gga caa gat tgt tat cgt    1206
Ser Gln Ile Pro Asn Cys Asp Met Ser His Gly Gln Asp Cys Tyr Arg
        380                 385                 390 ggg aat ggc aaa aat tat atg ggc aac tta tcc caa aca aga tct gga    1254
Gly Asn Gly Lys Asn Tyr Met Gly Asn Leu Ser Gln Thr Arg Ser Gly
395                 400                 405 cta aca tgt tca atg tgg gac aag aac atg gaa gac tta cat cgt cat    1302
Leu Thr Cys Ser Met Trp Asp Lys Asn Met Glu Asp Leu His Arg His
410                 415                 420                 425 atc ttc tgg gaa cca gat gca agt aag ctg aat gag aat tac tgc cga    1350
Ile Phe Trp Glu Pro Asp Ala Ser Lys Leu Asn Glu Asn Tyr Cys Arg
                430                 435                 440 aat cca gat gat gat gct cat gga ccc tgg tgc tac acg gga aat cca    1398
```

-continued

```
            Asn Pro Asp Asp Asp Ala His Gly Pro Trp Cys Tyr Thr Gly Asn Pro
                    445                 450                 455 ctc att cct tgg gat tat tgc cct att tct cgt tgt gaa ggt gat acc              1446
Leu Ile Pro Trp Asp Tyr Cys Pro Ile Ser Arg Cys Glu Gly Asp Thr
        460                 465                 470 aca cct aca ata gtc aat tta gac cat ccc gta ata tct tgt gcc aaa              1494
Thr Pro Thr Ile Val Asn Leu Asp His Pro Val Ile Ser Cys Ala Lys
475                 480                 485 acg aaa caa ttg cga gtt gta aat ggg att cca aca cga aca aac ata              1542
Thr Lys Gln Leu Arg Val Val Asn Gly Ile Pro Thr Arg Thr Asn Ile
490                 495                 500                 505 gga tgg atg gtt agt ttg aga tac aga aat aaa cat atc tgc gga gga              1590
Gly Trp Met Val Ser Leu Arg Tyr Arg Asn Lys His Ile Cys Gly Gly
            510                 515                 520 tca ttg ata aag gag agt tgg gtt ctt act gca cga cag tgt ttc cct              1638
Ser Leu Ile Lys Glu Ser Trp Val Leu Thr Ala Arg Gln Cys Phe Pro
        525                 530                 535 tct cga gac ttg aaa gat tat gaa gct tgg ctt gga att cat gat gtc              1686
Ser Arg Asp Leu Lys Asp Tyr Glu Ala Trp Leu Gly Ile His Asp Val
    540                 545                 550 cac gga aga gga gat gag aaa tgc aaa cag gtt ctc aat gtt tcc cag              1734
His Gly Arg Gly Asp Glu Lys Cys Lys Gln Val Leu Asn Val Ser Gln
555                 560                 565 ctg gta tat ggc cct gaa gga tca gat ctg gtt tta atg aag ctt gcc              1782
Leu Val Tyr Gly Pro Glu Gly Ser Asp Leu Val Leu Met Lys Leu Ala
570                 575                 580                 585 agg cct gct gtc ctg gat gat ttt gtt agt acg att gat tta cct aat              1830
Arg Pro Ala Val Leu Asp Asp Phe Val Ser Thr Ile Asp Leu Pro Asn
            590                 595                 600 tat gga tgc aca att cct gaa aag acc agt tgc agt gtt tat ggc tgg              1878
Tyr Gly Cys Thr Ile Pro Glu Lys Thr Ser Cys Ser Val Tyr Gly Trp
        605                 610                 615 ggc tac act gga ttg atc aac tat gat ggc cta tta cga gtg gca cat              1926
Gly Tyr Thr Gly Leu Ile Asn Tyr Asp Gly Leu Leu Arg Val Ala His
    620                 625                 630 ctc tat ata atg gga aat gag aaa tgc agc cag cat cat cga ggg aag              1974
Leu Tyr Ile Met Gly Asn Glu Lys Cys Ser Gln His His Arg Gly Lys
635                 640                 645 gtg act ctg aat gag tct gaa ata tgt gct ggg gct gaa aag att gga              2022
Val Thr Leu Asn Glu Ser Glu Ile Cys Ala Gly Ala Glu Lys Ile Gly
650                 655                 660                 665 tca gga cca tgt gag ggg gat tat ggt ggc cca ctt gtt tgt gag caa              2070
Ser Gly Pro Cys Glu Gly Asp Tyr Gly Gly Pro Leu Val Cys Glu Gln
            670                 675                 680 cat aaa atg aga atg gtt ctt ggt gtc att gtt cct ggt cgt gga tgt              2118
His Lys Met Arg Met Val Leu Gly Val Ile Val Pro Gly Arg Gly Cys
        685                 690                 695 gcc att cca aat cgt cct ggt att ttt gtc cga gta gca tat tat gca              2166
Ala Ile Pro Asn Arg Pro Gly Ile Phe Val Arg Val Ala Tyr Tyr Ala
    700                 705                 710 aaa tgg ata cac aaa att att tta aca tat aag gta cca cag tca tag              2214
Lys Trp Ile His Lys Ile Ile Leu Thr Tyr Lys Val Pro Gln Ser
715                 720                 725

<210> SEQ ID NO 2
<211> LENGTH: 728
<212> TYPE: PRT
<213> ORGANISM: Homo sapiens
<223> OTHER INFORMATION: HGF-A (Full length HGF)

<400> SEQUENCE: 2
```

-continued

```
Met Trp Val Thr Lys Leu Leu Pro Ala Leu Leu Gln His Val Leu
 1               5                  10                  15

Leu His Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
        50                  55                  60

Asn Thr Ala Asp Gln Cys Ala Asn Arg Cys Thr Arg Asn Lys Gly Leu
 65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
            115                 120                 125

Ile Ile Gly Lys Gly Arg Ser Tyr Lys Gly Thr Val Ser Ile Thr Lys
        130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
        290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415
```

```
Lys Asn Met Glu Asp Leu His Arg His Ile Phe Trp Glu Pro Asp Ala
        420                 425                 430

Ser Lys Leu Asn Glu Asn Tyr Cys Arg Asn Pro Asp Asp Ala His
        435                 440                 445

Gly Pro Trp Cys Tyr Thr Gly Asn Pro Leu Ile Pro Trp Asp Tyr Cys
        450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
                500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
        530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
                580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
        610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
                660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
        690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 3
<211> LENGTH: 2199
<212> TYPE: DNA
<213> ORGANISM: Homo sapiens
<220> FEATURE:
<221> NAME/KEY: CDS
<222> LOCATION: (28)..(2196)
<223> OTHER INFORMATION: HGF-B (five amino acids deletion type)

<400> SEQUENCE: 3
ggatccgcca gcccgtccag cagcacc atg tgg gtg acc aaa ctc ctg cca gcc      54
                                Met Trp Val Thr Lys Leu Leu Pro Ala
                                 1               5 ctg ctg ctg cag cat gtc ctc ctg cat ctc ctc ctg ctc ccc atc gcc      102
Leu Leu Leu Gln His Val Leu Leu His Leu Leu Leu Leu Pro Ile Ala
 10                  15                  20                  25
```

```
atc ccc tat gca gag gga caa agg aaa aga aga aat aca att cat gaa      150
Ile Pro Tyr Ala Glu Gly Gln Arg Lys Arg Arg Asn Thr Ile His Glu
             30                  35                  40 ttc aaa aaa tca gca aag act acc cta atc aaa ata gat cca gca ctg      198
Phe Lys Lys Ser Ala Lys Thr Thr Leu Ile Lys Ile Asp Pro Ala Leu
             45                  50                  55 aag ata aaa acc aaa aaa gtg aat act gca gac caa tgt gct aat aga      246
Lys Ile Lys Thr Lys Lys Val Asn Thr Ala Asp Gln Cys Ala Asn Arg
             60                  65                  70 tgt act agg aat aaa gga ctt cca ttc act tgc aag gct ttt gtt ttt      294
Cys Thr Arg Asn Lys Gly Leu Pro Phe Thr Cys Lys Ala Phe Val Phe
         75                  80                  85 gat aaa gca aga aaa caa tgc ctc tgg ttc ccc ttc aat agc atg tca      342
Asp Lys Ala Arg Lys Gln Cys Leu Trp Phe Pro Phe Asn Ser Met Ser
         90                  95                 100                 105 agt gga gtg aaa aaa gaa ttt ggc cat gaa ttt gac ctc tat gaa aac      390
Ser Gly Val Lys Lys Glu Phe Gly His Glu Phe Asp Leu Tyr Glu Asn
                 110                 115                 120 aaa gac tac att aga aac tgc atc att ggt aaa gga cgc agc tac aag      438
Lys Asp Tyr Ile Arg Asn Cys Ile Ile Gly Lys Gly Arg Ser Tyr Lys
             125                 130                 135 gga aca gta tct atc act aag agt ggc atc aaa tgt cag ccc tgg agt      486
Gly Thr Val Ser Ile Thr Lys Ser Gly Ile Lys Cys Gln Pro Trp Ser
             140                 145                 150 tcc atg ata cca cac gaa cac agc tat cgg ggt aaa gac cta cag gaa      534
Ser Met Ile Pro His Glu His Ser Tyr Arg Gly Lys Asp Leu Gln Glu
         155                 160                 165 aac tac tgt cga aat cct cga ggg gaa gaa ggg gga ccc tgg tgt ttc      582
Asn Tyr Cys Arg Asn Pro Arg Gly Glu Glu Gly Gly Pro Trp Cys Phe
170                 175                 180                 185 aca agc aat cca gag gta cgc tac gaa gtc tgt gac att cct cag tgt      630
Thr Ser Asn Pro Glu Val Arg Tyr Glu Val Cys Asp Ile Pro Gln Cys
                 190                 195                 200 tca gaa gtt gaa tgc atg acc tgc aat ggg gag agt tat cga ggt ctc      678
Ser Glu Val Glu Cys Met Thr Cys Asn Gly Glu Ser Tyr Arg Gly Leu
             205                 210                 215 atg gat cat aca gaa tca ggc aag att tgt cag cgc tgg gat cat cag      726
Met Asp His Thr Glu Ser Gly Lys Ile Cys Gln Arg Trp Asp His Gln
             220                 225                 230 aca cca cac cgg cac aaa ttc ttg cct gaa aga tat ccc gac aag ggc      774
Thr Pro His Arg His Lys Phe Leu Pro Glu Arg Tyr Pro Asp Lys Gly
         235                 240                 245 ttt gat gat aat tat tgc cgc aat ccc gat ggc cag ccg agg cca tgg      822
Phe Asp Asp Asn Tyr Cys Arg Asn Pro Asp Gly Gln Pro Arg Pro Trp
250                 255                 260                 265 tgc tat act ctt gac cct cac acc cgc tgg gag tac tgt gca att aaa      870
Cys Tyr Thr Leu Asp Pro His Thr Arg Trp Glu Tyr Cys Ala Ile Lys
                 270                 275                 280 aca tgc gct gac aat act atg aat gac act gat gtt cct ttg gaa aca      918
Thr Cys Ala Asp Asn Thr Met Asn Asp Thr Asp Val Pro Leu Glu Thr
             285                 290                 295 act gaa tgc atc caa ggt caa gga gaa ggc tac agg ggc act gtc aat      966
Thr Glu Cys Ile Gln Gly Gln Gly Glu Gly Tyr Arg Gly Thr Val Asn
             300                 305                 310 acc att tgg aat gga att cca tgt cag cgt tgg gat tct cag tat cct     1014
Thr Ile Trp Asn Gly Ile Pro Cys Gln Arg Trp Asp Ser Gln Tyr Pro
         315                 320                 325 cac gag cat gac atg act cct gaa aat ttc aag tgc aag gac cta cga     1062
His Glu His Asp Met Thr Pro Glu Asn Phe Lys Cys Lys Asp Leu Arg
```

```
                 330                 335                 340                 345
gaa aat tac tgc cga aat cca gat ggg tct gaa tca ccc tgg tgt ttt        1110
Glu Asn Tyr Cys Arg Asn Pro Asp Gly Ser Glu Ser Pro Trp Cys Phe
                350                 355                 360 acc act gat cca aac atc cga gtt ggc tac tgc tcc caa att cca aac        1158
Thr Thr Asp Pro Asn Ile Arg Val Gly Tyr Cys Ser Gln Ile Pro Asn
                365                 370                 375 tgt gat atg tca cat gga caa gat tgt tat cgt ggg aat ggc aaa aat        1206
Cys Asp Met Ser His Gly Gln Asp Cys Tyr Arg Gly Asn Gly Lys Asn
                380                 385                 390 tat atg ggc aac tta tcc caa aca aga tct gga cta aca tgt tca atg        1254
Tyr Met Gly Asn Leu Ser Gln Thr Arg Ser Gly Leu Thr Cys Ser Met
            395                 400                 405 tgg gac aag aac atg gaa gac tta cat cgt cat atc ttc tgg gaa cca        1302
Trp Asp Lys Asn Met Glu Asp Leu His Arg His Ile Phe Trp Glu Pro
410                 415                 420                 425 gat gca agt aag ctg aat gag aat tac tgc cga aat cca gat gat gat        1350
Asp Ala Ser Lys Leu Asn Glu Asn Tyr Cys Arg Asn Pro Asp Asp Asp
                430                 435                 440 gct cat gga ccc tgg tgc tac acg gga aat cca ctc att cct tgg gat        1398
Ala His Gly Pro Trp Cys Tyr Thr Gly Asn Pro Leu Ile Pro Trp Asp
                445                 450                 455 tat tgc cct att tct cgt tgt gaa ggt gat acc aca cct aca ata gtc        1446
Tyr Cys Pro Ile Ser Arg Cys Glu Gly Asp Thr Thr Pro Thr Ile Val
                460                 465                 470 aat tta gac cat ccc gta ata tct tgt gcc aaa acg aaa caa ttg cga        1494
Asn Leu Asp His Pro Val Ile Ser Cys Ala Lys Thr Lys Gln Leu Arg
            475                 480                 485 gtt gta aat ggg att cca aca cga aca aac ata gga tgg atg gtt agt        1542
Val Val Asn Gly Ile Pro Thr Arg Thr Asn Ile Gly Trp Met Val Ser
490                 495                 500                 505 ttg aga tac aga aat aaa cat atc tgc gga gga tca ttg ata aag gag        1590
Leu Arg Tyr Arg Asn Lys His Ile Cys Gly Gly Ser Leu Ile Lys Glu
                510                 515                 520 agt tgg gtt ctt act gca cga cag tgt ttc cct tct cga gac ttg aaa        1638
Ser Trp Val Leu Thr Ala Arg Gln Cys Phe Pro Ser Arg Asp Leu Lys
                525                 530                 535 gat tat gaa gct tgg ctt gga att cat gat gtc cac gga aga gga gat        1686
Asp Tyr Glu Ala Trp Leu Gly Ile His Asp Val His Gly Arg Gly Asp
                540                 545                 550 gag aaa tgc aaa cag gtt ctc aat gtt tcc cag ctg gta tat ggc cct        1734
Glu Lys Cys Lys Gln Val Leu Asn Val Ser Gln Leu Val Tyr Gly Pro
            555                 560                 565 gaa gga tca gat ctg gtt tta atg aag ctt gcc agg cct gct gtc ctg        1782
Glu Gly Ser Asp Leu Val Leu Met Lys Leu Ala Arg Pro Ala Val Leu
570                 575                 580                 585 gat gat ttt gtt agt acg att gat tta cct aat tat gga tgc aca att        1830
Asp Asp Phe Val Ser Thr Ile Asp Leu Pro Asn Tyr Gly Cys Thr Ile
                590                 595                 600 cct gaa aag acc agt tgc agt gtt tat ggc tgg ggc tac act gga ttg        1878
Pro Glu Lys Thr Ser Cys Ser Val Tyr Gly Trp Gly Tyr Thr Gly Leu
            605                 610                 615 atc aac tat gat ggc cta tta cga gtg gca cat ctc tat ata atg gga        1926
Ile Asn Tyr Asp Gly Leu Leu Arg Val Ala His Leu Tyr Ile Met Gly
                620                 625                 630 aat gag aaa tgc agc cag cat cat cga ggg aag gtg act ctg aat gag        1974
Asn Glu Lys Cys Ser Gln His His Arg Gly Lys Val Thr Leu Asn Glu
            635                 640                 645 tct gaa ata tgt gct ggg gct gaa aag att gga tca gga cca tgt gag        2022
```

-continued

```
Ser Glu Ile Cys Ala Gly Ala Glu Lys Ile Gly Ser Gly Pro Cys Glu
650                 655                 660                 665 ggg gat tat ggt ggc cca ctt gtt tgt gag caa cat aaa atg aga atg     2070
Gly Asp Tyr Gly Gly Pro Leu Val Cys Glu Gln His Lys Met Arg Met
                    670                 675                 680 gtt ctt ggt gtc att gtt cct ggt cgt gga tgt gcc att cca aat cgt     2118
Val Leu Gly Val Ile Val Pro Gly Arg Gly Cys Ala Ile Pro Asn Arg
                685                 690                 695 cct ggt att ttt gtc cga gta gca tat tat gca aaa tgg ata cac aaa     2166
Pro Gly Ile Phe Val Arg Val Ala Tyr Tyr Ala Lys Trp Ile His Lys
            700                 705                 710 att att tta aca tat aag gta cca cag tca tag                         2199
Ile Ile Leu Thr Tyr Lys Val Pro Gln Ser
        715                 720
```

<210> SEQ ID NO 4
<211> LENGTH: 723
<212> TYPE: PRT
<213> ORGANISM: Homo sapiens
<223> OTHER INFORMATION: HGF-B (five amino acids deletion type)

<400> SEQUENCE: 4

```
Met Trp Val Thr Lys Leu Leu Pro Ala Leu Leu Leu Gln His Val Leu
 1               5                  10                  15

Leu His Leu Leu Leu Pro Ile Ala Ile Pro Tyr Ala Glu Gly Gln
                20                  25                  30

Arg Lys Arg Arg Asn Thr Ile His Glu Phe Lys Lys Ser Ala Lys Thr
            35                  40                  45

Thr Leu Ile Lys Ile Asp Pro Ala Leu Lys Ile Lys Thr Lys Lys Val
        50                  55                  60

Asn Thr Ala Asp Gln Cys Ala Asn Arg Cys Thr Arg Asn Lys Gly Leu
 65                 70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
            115                 120                 125

Ile Ile Gly Lys Gly Arg Ser Tyr Lys Gly Thr Val Ser Ile Thr Lys
        130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
            180                 185                 190

Tyr Glu Val Cys Asp Ile Pro Gln Cys Ser Glu Val Glu Cys Met Thr
        195                 200                 205

Cys Asn Gly Glu Ser Tyr Arg Gly Leu Met Asp His Thr Glu Ser Gly
    210                 215                 220

Lys Ile Cys Gln Arg Trp Asp His Gln Thr Pro His Arg His Lys Phe
225                 230                 235                 240

Leu Pro Glu Arg Tyr Pro Asp Lys Gly Phe Asp Asp Asn Tyr Cys Arg
                245                 250                 255

Asn Pro Asp Gly Gln Pro Arg Pro Trp Cys Tyr Thr Leu Asp Pro His
            260                 265                 270
```

```
Thr Arg Trp Glu Tyr Cys Ala Ile Lys Thr Cys Ala Asp Asn Thr Met
        275                 280                 285
Asn Asp Thr Asp Val Pro Leu Glu Thr Thr Glu Cys Ile Gln Gly Gln
    290                 295                 300
Gly Glu Gly Tyr Arg Gly Thr Val Asn Thr Ile Trp Asn Gly Ile Pro
305                 310                 315                 320
Cys Gln Arg Trp Asp Ser Gln Tyr Pro His Glu His Asp Met Thr Pro
                325                 330                 335
Glu Asn Phe Lys Cys Lys Asp Leu Arg Glu Asn Tyr Cys Arg Asn Pro
            340                 345                 350
Asp Gly Ser Glu Ser Pro Trp Cys Phe Thr Thr Asp Pro Asn Ile Arg
        355                 360                 365
Val Gly Tyr Cys Ser Gln Ile Pro Asn Cys Asp Met Ser His Gly Gln
    370                 375                 380
Asp Cys Tyr Arg Gly Asn Gly Lys Asn Tyr Met Gly Asn Leu Ser Gln
385                 390                 395                 400
Thr Arg Ser Gly Leu Thr Cys Ser Met Trp Asp Lys Asn Met Glu Asp
                405                 410                 415
Leu His Arg His Ile Phe Trp Glu Pro Asp Ala Ser Lys Leu Asn Glu
            420                 425                 430
Asn Tyr Cys Arg Asn Pro Asp Asp Ala His Gly Pro Trp Cys Tyr
        435                 440                 445
Thr Gly Asn Pro Leu Ile Pro Trp Asp Tyr Cys Pro Ile Ser Arg Cys
    450                 455                 460
Glu Gly Asp Thr Thr Pro Thr Ile Val Asn Leu Asp His Pro Val Ile
465                 470                 475                 480
Ser Cys Ala Lys Thr Lys Gln Leu Arg Val Val Asn Gly Ile Pro Thr
                485                 490                 495
Arg Thr Asn Ile Gly Trp Met Val Ser Leu Arg Tyr Arg Asn Lys His
            500                 505                 510
Ile Cys Gly Gly Ser Leu Ile Lys Glu Ser Trp Val Leu Thr Ala Arg
        515                 520                 525
Gln Cys Phe Pro Ser Arg Asp Leu Lys Asp Tyr Glu Ala Trp Leu Gly
    530                 535                 540
Ile His Asp Val His Gly Arg Gly Asp Glu Lys Cys Lys Gln Val Leu
545                 550                 555                 560
Asn Val Ser Gln Leu Val Tyr Gly Pro Glu Gly Ser Asp Leu Val Leu
                565                 570                 575
Met Lys Leu Ala Arg Pro Ala Val Leu Asp Asp Phe Val Ser Thr Ile
            580                 585                 590
Asp Leu Pro Asn Tyr Gly Cys Thr Ile Pro Glu Lys Thr Ser Cys Ser
        595                 600                 605
Val Tyr Gly Trp Gly Tyr Thr Gly Leu Ile Asn Tyr Asp Gly Leu Leu
    610                 615                 620
Arg Val Ala His Leu Tyr Ile Met Gly Asn Glu Lys Cys Ser Gln His
625                 630                 635                 640
His Arg Gly Lys Val Thr Leu Asn Glu Ser Glu Ile Cys Ala Gly Ala
                645                 650                 655
Glu Lys Ile Gly Ser Gly Pro Cys Glu Gly Asp Tyr Gly Gly Pro Leu
            660                 665                 670
Val Cys Glu Gln His Lys Met Arg Met Val Leu Gly Val Ile Val Pro
        675                 680                 685
Gly Arg Gly Cys Ala Ile Pro Asn Arg Pro Gly Ile Phe Val Arg Val
```

-continued

```
                690                 695                 700
Ala Tyr Tyr Ala Lys Trp Ile His Lys Ile Ile Leu Thr Tyr Lys Val
705                 710                 715                 720
Pro Gln Ser
```

TREATMENT OF NEURONS WITH HGF

This application is the National Stage of International Application No. PCT/JP94/01533, filed Sep. 16, 1994.

TECHNICAL FIELD

The present invention relates to a therapeutic agent for disorder in brain and nerve. More particularly, it relates to a therapeutic agent for disorder in brain and nerve containing HGF (hepatocyte growth factor) as an active ingredient.

BACKGROUND ART

HGF is a protein discovered by the present inventor in the serum of rats with a regenerating liver as a factor inducing proliferation of mature hepatic parenchymal cells in vitro (Biochem. Biophys. Res. Commun., 122, 1450, 1984). The inventor further succeeded in isolating HGF from rat platelets (Proc. Natl. Acad. Sci., 83, 6489, 1986, FEBS Letter, 22, 311, 1987), and determined a part of its amino acid sequences. On the basis of the clarified amino acid sequences of HGF, the inventor carried out cloning of human and rat HGF cDNAs, and succeeded in obtaining the hepatic parenchymal cell growth factor as a recombinant protein using the cDNA in animal cells (human HGF: Nature, 342, 440, 1989; rat HGF: Proc. Natl. Acad. Sci., 87, 3200, 1990).

The molecular weight of HGF is 82 to 85 kD in SDS-polyacrylamide gel electrophoresis. The rat HGF molecule has a heterodimer structure of α-chain composed of 463 amino acid residues and β-chain composed of 233 amino acid residues, and both α-chain and β-chain are crosslinked to each other with one disulfide bond and have two glucosamine-type sugar chain binding sites. The human HGF also possesses almost the same physiological activity, and has α-chain composed of 463 amino acid residues and β-chain composed of 234 amino acid residues. The α-chain has 4 kringle structures similar to that of fibrinolytic enzyme plasmin, and the amino acid sequence of β-chain has about 37% homology with β-chain of plasmin having serine protease activity. The homology of amino acid sequence between rat HGF and human HGF is very high, i.e. 91.6% in α-chain and 88.9% in β-chain, and their activities can be utterly exchangeable.

HGF discovered as a factor for specifically proliferating the hepatic parenchymal cells has been disclosed to show various activities in the body as a result of recent studies by the inventor and other researchers, and it is expected to be applied in remedies for humans and animals, as well as the subject of study.

The inventor proved that HGF acts as a growth factor not only on hepatocytes but also widely on epithelial cells, and have completed several inventions. In Japanese Patent Kokai No. 49246/1992, the inventor described the development and application of HGF as a medicine for renal diseases on the basis of the action of HGF to promote cell proliferation in proximal tubule of the kidney. On the basis of the HGF action to promote proliferation of normal epithelial cells such as melanocytes and keratinocytes, the inventor also described in Japanese Patent Application No. 419158/1990, the development and application of HGF as an epithelial cell growth accelerator for wound healing and skin ulcer treatment or as a medicine for the proliferation of hair root cells. In particular, HGF does not have carcinogenic effect and the activity of promoting the proliferation of cancer cells, which are observed with many growth factors such as EGF, and hence it is more practicable. The inventor, moreover, in Japanese Patent Kokai No. 25010/1994, described that HGF could be used as an anti-cancer agent utilizing the property of HGF to inhibit the proliferation of cancer cells such as HepG2 cell line derived from a human hepatoma, IM9 cell line derived from lymphoblast tumor and the like.

More recently, the inventor discovered that HGF promotes regeneration in injured lung, and that the plasma HGF level in patients with lung diseases is far higher than that in normal subjects (Yanagita et al., Biochem. Biophys. Res. Commun., 182, 802–809, 1992).

Relating to the receptor of the HGF, it has been identified from the recent studies that c-met proto oncogene codes the HGF receptor (Bottaro et al., Science 251, 802–804, 1991; Naldini et al., Oncogene 6, 501–504, 1991).

Another important point in considering the practical use of HGF as medicine is that HGF promotes the growth of cells only in phase G1, that is, the cells only in the growth period, not cells in phase G0, that is, stationary period. It means that it promotes growth and regeneration of injured tissues, but does not act at all on intact tissues. Therefore, if HGF is administered excessively, or if HGF reaches non-ailing sites through blood or the like, it does not induce carcinogenic action or excessive growth in normal tissues.

Since HGF widely promotes growth of epithelial cells, as well as hepatocytes, and has the growth inhibitory activity for cancer cells, it is expected that HGF acts to heal tissue injuries in the body. HGF producing cells are not epithelial cells themselves, but it is elucidated that HGF is produced mainly by mesenchymal cells, for example, Kupffer cells and vascular endothelial cells of sinusoidal wall in the liver, capillary endothelial cells in the kidney, alveolar macrophage and vascular endothelial cells in the lung, and it has been elucidated that HGF is supplied from adjacent cells when required, and the so-called paracrine mechanism is established.

However, when the liver or kidney is injured, production of HGF is increased also in intact organs such as the lung, and it is estimated that HGF is supplied also by the so-called endocrine mechanism.

Thus, the HGF is a growth factor acting to heal wounds in various organs and tissues, but in the event of disorder in brain and nerve, it has not been known whether HGF contributes to restoration of brain and nerve injuries or not. Accordingly, the inventor studied the action of HGF in the brains and nerves, and found that survival of brain and nerve cells is promoted by HGF, and that expression of HGF mRNA and c-met mRNA in the brains is evidently increased in the body having brain injury.

The invention is based on such findings, and it is hence a primary object of the invention to present a useful therapeutic agent for disorder in brain and nerve for prevention and treatment of disorder in brain and nerve.

DISCLOSURE OF THE INVENTION

The invention relates to a therapeutic agent for disorder in brain and nerve containing an effective amount of HGF and if necessary, a pharmacologically acceptable carrier.

Other aspects of the invention include a method of treatment of disorder in brain and nerve of humans or mammals by administering an effective amount of HGF; a use of HGF for manufacturing a therapeutic agent for disorder in brain and nerve; an agent promoting survival of brain and nerve cells containing an effective amount of HGF and if necessary, a pharmacologically acceptable carrier; a method of promoting survival of brain and nerve cells of humans or mammals by administering an effective amount of HGF; and a use of HGF for manufacturing an agent promoting a survival of brain and nerve cells of humans or mammals.

HGF as described above may be derived from either human or animal tissue or blood components, or manufactured by recombinant DNA technique.

HGF, the active ingredient, possesses an action for promoting survival of brain and nerve cells, and hence can regenerate and restore the insured brains and nerves.

BRIEF DESCRIPTION OF THE DRAWINGS

FIGS. 3A–B are graphs showing effects of HGF and other growth factors on the growth of PC12 cells. In the graphs, A shows the promoting effect of HGF on growth of PC12 cells, B shows the effects of HGF, EGF, NGF, and their combination on growth of PC12 cells.

FIGS. 4A–F are a graph showing the effect of HGF to promote survival of PC12 cells.

FIGS. 6A–B are graphs showing the results of binding experiment of $^{125}$I-HGF to PC12 cells cultured in the presence or absence of NGF. In the graphs, A represents the saturation curve of specific binding of $^{125}$I-HGF to PC12 cells cultured in the absence of NGF (●) or in the presence of 50 ng/ml of NGF (○), and B represents Scatchard plot of the binding of $^{125}$I-HGF to PC12 cells.

BEST MODES OF CARRYING OUT THE INVENTION

Figure 1:
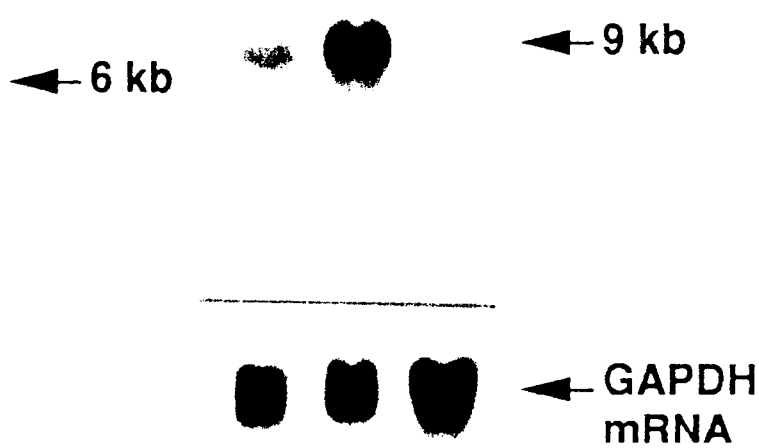
FIG. 1 is a photograph of Northern blot analysis when RNA was electrophoresed in agarose/formaldehyde gel, showing changes of HGF mRNA and c-met mRNA levels in the brain of rats from late-fetal to adult stages.

As to HGF which is the active ingredient of the invention, any HGF can be used in the invention as long as it is purified to be able to use for a medicine, regardless of preparation methods of HGF. Many methods are known to prepare HGF, and, for example, HGF can be obtained by extraction and purification from organs such as liver, spleen, lung, bone marrow, brain, kidney, placenta and the like, blood cells such as platelets, leukocytes and the like, plasma and serum of mammals such as rat, cow, horse, sheep and the like. Also, it is possible to obtain HGF by cultivation of primary culture cells or cell lines producing HGF, followed by separation and purification from the culture product (e.g. culture supernatant, cultured cell, etc.). Further, HGF can be obtained by gene engineering method which comprises recombining the gene coding HGF with a proper vector, inserting it into a proper host cell to give a transformant, and separating the desired recombinant HGF from the culture supernatant of the transformant (e.g. Nature, 342, 440, 1989, Japanese Patent Kokai No. 111383/1993, Biochem. Biophys. Res. Commun., 163, 967, 1989). The host cell is not specifically limited, and various host cells conventionally used in gene engineering methods can be used, which are, for example, *Escherichia coli, Bacillus subtilis,* yeast, filamentous fungi, and plant or animal cells.

More specifically, the method of extracting and purifying HGF from live tissues is, for example, to administer carbon tetrachloride to a rat intraperitoneally, remove a liver from the rat with hepatitis, grind it, and purify by the ordinary protein purifying technique such as gel column chromatography using S-Sepharose and heparin Sepharose, HPLC and the like. Further, by the gene engineering method, the gene coding the amino acid sequence of human HGF is recombined with a vector such as bovine papilloma virus DNA and the like to obtain an expression vector, and by using this expression vector, animals cells such as Chinese hamster ovary (CHO) cells, mouse C127 cells, monkey COS cells and the like are transformed, and HGF can be obtained from the culture supernatant of the transformants.

As to HGF thus obtained, there are possibilities that a part of the amino acid sequence will be deleted or substituted with other amino acid(s), that another amino acid sequence is partially inserted, that 1, 2 or more amino acids are attached to the C and/or N terminals, or that sugars are similarly deleted or substituted. Such HGF analogues which are encompassed by the present invention are disclosed in Japanese Patent Kokai No. 130091/1992 and PCT International Publication No. WO90/10651, and they may be also used in the invention and are included within the scope of the invention.

HGF, the active ingredient of the therapeutic agent of the invention, possesses the action of promoting survival of brain and nerve cells as shown in Examples below, and it is also known to increase evidently the expression of HGF mRNA and c-met/HGF receptor mRNA in the brain in the body having a injury to brain.

More specifically. HGF mRNA and c-met mRNA were expressed in the brains of late-fetal, neonatal and adult rats. Both HGF mRNA and c-met mRNA were widely expressed in the entire brain of adult rat, and distributions of relatively high level of their expressions were noted in hippocampus, olfactory bulb and their related regions. Similarity of distribution between HGF mRNA and c-met mRNA suggests that HGF plays the role in the brain, same as in the liver, kidney and lung.

Although HGF has been shown to regulate growth, motility and morphogenesis of various types of cells, whether neuronal-type of cells respond to HGF has been unknown. Rat pheochromocytoma PC12 cells are cells derived from neural crest, and have an adrenergic property (Greene et al., Proc. Natl. Acad. Sci., 73, 2424–2428, 1976). The PC12 cells have been widely used in the study of neurotrophic factor-induced differentiation. The cells show many of the properties of adrenal medullary chromaffin cells and by culturing in the presence of NGF, fibroblast growth factor (FGF) or interleukin 6 (IL-6), the cells show a program of physiological changes, resulting in phenotype resembling that of sympathetic nerve cells (Togari et al., Biochem. Biophys. Res. Commun, 114, 1189–1193, 1983).

Although HGF did not stimulate the DNA synthesis of PC12 cells, HGF stimulated viability of PC12 cells, which resulted in prolonged survival. It may be, therefore, concluded that HGF functions as a survival factor for PC12 cells, rather than mitogen. This ability to prolong survival of nerve cells (neurons) is a novel biological activity of HGF.

Same as the result disclosed in literature (Greene et al., Proc. Natl. Acad. Sci., 73, 9244–2428, 1976), NGF inhibited the DNA synthesis and proliferation of PC12 cells while induced their differentiation. Since NGF is known to prevent the death of PC12 cells in serum-free culture medium (Greene, L., J. Cell Biol., 78, 747–755, 1978), NGF maintains the survival of PC12 cells with differentiated phenotype. In contrast to NGF, although HGF had no effect on DNA synthesis of PC12 cells, HGF enhanced cell growth presumably through its remarkable ability to prolong the survival of PC12 cells. Therefore, HGF promotes the survival of PC12 cells through different pathway from NGF and the effect of HGF seems to be similar to that of EGF. However, since the effects on HGF and EGF appeared to be additive in growth promoting activity, these factors seem to regulate growth and survival of PC12 cells through similar but different intracellular signaling pathway.

The presence of high affinity HGF receptor on PC12 cells (185 sites/cell with Kd of 40 pM) clearly indicates that PC12 cells are target cell of HGF and prolonged survival of PC12 cells is mediated through high affinity receptor. On the other hand, induction of differentiation in PC12 cells by NGF accompanied marked decrease in the number of HGF receptor. As known from this result of experiment, HGF may exert its biological activities for the undifferentiated PC12 cells rather than for the differentiated cells. Such differentiation-related decrease in growth factor receptor on PC12 cells was also noted in the report of EGF (Huff et al., Biochem. Biophys. Res. Commun., 89, 178–180, 1979, etc.). Accordingly, it is possible to speculate that alteration of PC12 cells from proliferative to differentiative phase may accompany the unavailability of growth factor receptors and such charges may lead the difference in responsiveness of undifferentiated and differentiated cells to growth factors. T98G, GOTO and SCCH-26 cells derived from central nervous tissues also express high affinity HGF receptor. HGF did not stimulate DNA synthesis of these cells, but these cells may have potential to respond to HGF.

It is a completely novel finding that HGF prolonged survival of hippocampal neurons in primary culture, wherein these cells seem to maintain their original characters of nerve cells (neurons) in vivo. This result suggests that HGF may function as a survival factor for neurons also in vivo. As the phenomenon for supporting this fact, the expression of both HGF mRNA and c-met/HGF receptor mRNA markedly increased after ischemic lesions in adult rat brain.

As stated above, HGF seems to act as a "trophic-factor" for regeneration of various organs and tissues. Taken together with the results, HGF has a possible role as a "trophic-factor" in brain and nerve to prevent degenerative death of neurons and other cells and to prolong survival of nerve cells against various injuries in brain and nerves. The intrinsic biological activities of HGF (cell growth promotion, cell motility promotion, and morphological induction), and activities of HGF as a putative inducer on nervous tissues and as a survival factor on neurons all indicate that HGF is playing an extremely important role in tissue induction of brain and nerves, organogenesis and maintenance of homeostasis of body.

Thus, HGF has the action to prolong survival of brain and nerve cells, and in the body having injury in the brain or nerves, expression of HGF mRNA and c-met/HGF receptor mRNA increases significantly in the brain or nerves. Therefore, the therapeutic agent for disorder in brain and nerve of the invention is useful for nerve degeneration, cerebral stroke, cerebral infarction, dementia, cranial injury, peripheral neuropathy, diabetic neuropathy, neurotoxin induced lesions, injury of nerve cell by surgery, lesions of nerve cell by infection, tumor of nerve cell and the like. Herein, the nerve degeneration may be atrophic or degenerative dropout diseases of nerve cells, including, for example, Alzheimer's disease, senile dementia of Alzheimer type, amyotrophic lateral sclerosis, Parkinson's disease, Huntington's chorea and the like. The peripheral neuropathy includes, for example, lesions in optic nerve, sensory neurons, motor neurons, autonomic neurons and the like.

The therapeutic agent of the invention may be prepared in various preparation forms (for example, liquid, tablet, capsule), and generally it is prepared in the form of injection containing HGF as the active ingredient alone or together with common carrier, or in the form of oral preparation together with common carrier. The injection may be prepared by the conventional method, and for example, HGF is dissolved in a proper solvent (for example, sterilized water, buffer solution, physiological saline), filtered and sterilized, and put in a container aseptically. The content of HGF in the injection may be usually 0.0002 to 0.2 w/v %, preferably 0.001 to 0.1 w/v %. As oral preparation, it is manufactured in various preparation forms, including tablet, granule, fine granule, powder, soft or hard capsule, liquid, emulsion, suspension or syrup, and these preparations may be manufactured by the conventional method. The HGF content in the preparation may be properly adjusted depending on the preparation form and the disease to be treated.

In production of the preparation, it is preferable to add a stabilizer, and examples of the stabilizer include albumin, globulin, gelatin, mannitol, glucose, dextran, ethylene glycol and the like. Moreover, the preparation of the invention may contain other additives necessary for pharmaceutical preparation, such as an excipient, a dissolving aid, an antioxidant, a pain-alleviating agent, an agent for isotonicity and the like. In liquid preparation, it is preferable to store it under frozen conditions or after the removal of water by a process such as freeze-drying. The freeze-dried preparation is used by dissolving again in distilled water for injection and the like before use.

The preparation of the invention is administered through various routes depending on the preparation form. For example, the injection is administered by intrabrain, intravenous, intraarterial, subcutaneous, intramuscular and the like. The dose is adjusted properly depending on symptoms, age and body weight of patient, and generally 0.01 mg to 100 mg of HGF is administered once or several times per day.

INDUSTRIAL APPLICABILITY

In the therapeutic agent and method of treatment according to the invention, HGF which is the active ingredient prolongs survival of brain and nerve cells, and regenerates and restores the injured brain and nerves. Hence, the invention is useful for effectively preventing and treating various disorder in brain and nerve (e.g. dementia, Alzheimer's disease, senile dementia of Alzheimer type, amyotrophic lateral sclerosis, Parkinson's disease, cerebral stroke, cerebral infarction, cranial injury, etc).

EXAMPLE

The present invention is described in more detail referring to Examples and Preparation Examples. However, the invention is not limited to these examples. Materials and methods used in the following experiments are as follows:

Materials and Methods
(1) Materials

Male Wistar rats were used in the following experiments. Hybond-N, [α-$^{32}$P]dCTP and Na[$^{125}$I] and Megaprime DNA labeling system were obtained from Amersham Co. Biodyne-B was from Pall Co. (East Hills, N.Y.). Random primer DNA labeling kits and Oligotex dT30 (trademark) were purchased from Takara Co. (Kyoto) and Roche Pharmaceuticals (Tokyo), respectively.

(2) Growth Factors

Human recombinant HGF was purified from the conditioned medium of CHO cells transfected with human recombinant HGF cDNA (Nakamura, et al., Nature 342, 440–443, 1989 (SEQ ID NO:1, which encodes the protein of SEQ ID NO:2); Seki, et al., Biochem. Biophys. Res. Commun. 172, 321–327, 1990 (SEQ ID NO:3, which encodes the protein of SEQ ID NO:4)). 2.5S nerve growth factor (NGF) purified from mouse submaxillary glands was purchased from Biomedical Technology Inc. (Stoughton, MA). Human recombinant epidermal growth factor (EGF) was provided from Earth Pharmaceutical (Akoh, Japan).

(3) Northern Hybridization

For Northern analysis, total RNA was purified by the acid guanidinium thiocyanate-phenol-chloroform method. Total RNA was separated by 1.0% agarose/formaldehyde gel electrophoresis and transferred to a Biodyne-B nylon membrane.

EcoR1 fragment (1.4 kb) of rat HGF cDNA (RBC-1 clone which encodes the fourth kringle domain of α-chain, the entire β-chain, and a part of 3'-noncoding region), rat c-met cDNA (0.8 kb) or rat glutaraldehyde 3-phosphate dehydrogenase (GAPDH) cDNA which were prepared by polymerase-chain-reaction (PCR) amplification was labeled with [α-$^{32}$P]dCTP using the random primer DNA labeling kits or Megaprime DNA labeling system, and was used as a probe.

Hybridization were performed at 42° C. for 24 h in solution composed of 50% (w/v) formamide, 5×NaCl/Pi/EDTA (0.18 M NaCl, 10 mM NaH$_2$PO$_4$, pH 7.7, 1 mM Na$_2$EDTA), 2×Denhardt's, 1.0% SDS, 0.3% sodium N-lauroyl-sarcosinate and 100 µg/ml salmon sperm DNA. The membrane was washed with 0.2×NaCl/Pi/EDTA–0.1% SDS for 8 min at 65° C. then was autoradiographed on Fuji X-ray film, at –70° C. using intensifying screens.

(4) Cell Culture

PC12 rat pheochromocytoma, T98G human glioblastoma, GOTO and SCCH-26 human neuroblastoma cells were obtained from the Japanese Cancer Research Resources Bank. PC12 cells were cultured in RPMI1640 medium supplemented with 12% fetal calf serum (FCS). T98G cells were cultured in Eagle's minimum essential medium (MEM) supplemented with non-essential amino acids (8.9 mg/liter L-alanine, 15.0 mg/liter L-asparagine, 13.3 mg/liter L-aspartic acid, 14.7 mg/liter L-glutamic acid, 11.5 mg/liter L-proline, 10.5 mg/liter L-serine, and 7.5 mg/liter glycine), 1.1 mg/ml pyruvate and 10% FCS. GOTO cells were cultured in mixture of RPMI1640 and MEM medium (1:1) supplemented with 10% FCS. SCCH-26 cells were cultured in ES medium supplemented with 10% FCS.

(5) Radioiodin [$^{125}$I]-labeling of HGF

Human recombinant HGF was radioiodinated by the chloramine-T method. Details on the methods for the radioiodination were described previously (Higuchi & Nakamura, Biochem. Biophys. Res. Commun. 176, 599–607, 1991). Briefly, 1.5 M sodium phosphate buffer, pH 7.0 (10 µl), 0.5 µg HGF (17 µl), and 0.5 mCi Na[$^{125}$I] (14Ci/mg I, IMS 30) were mixed in a siliconized tube and the reaction was started by adding 5 µl of chloramine-T solution (100 µg/ml), four times at 30 s intervals. The reaction was stopped by adding 20 µl of 50 mM N-acetyl-L-tyrosine (Sigma Co.), 200 µl of 60 mM potassium iodide and 200 µl of urea solution (1.2 g/ml in 1 M acetic acid). $^{125}$I-HGF was separated by molecular sieve chromatography on a Sephadex G-25 column (Pharmacia Co.) equilibrated with 4 mM HCl, 75 mM NaCl, and 1 mg/ml bovine serum albumin (BSA, Sigma Co.). $^{125}$I-HGF thus prepared had a specific activity of 70–160 mCi/mg protein.

(6) $^{125}$I-HGF Binding Assay

The binding assay on cultured cells was carried out as follows. PC12, T98G, GOTO, SCCH-26 cells were detached from culture plates by extremely short-term treatment with trypsin. The cell suspension were incubated at 10° C. for 1 h in binding buffer containing various concentrations of $^{125}$I-HGF, with or without excess amounts of unlabeled HGF, in siliconized tubes (Assist Co.). The cells were overlaid onto an oil cushion composed of di-n-butyl phthalate and di-(2-ethylhexyl) phthalate (3:2) and centrifuged for 5 min at 12,000 g at 4° C. After discarding the aqueous and oil phases, $^{125}$I-HGF specifically bound to the cell pellet was counted in a γ-counter. All binding experiments were done in triplicate.

(7) Measurement of Cell Growth, Survival, and DNA Synthesis of PC12 Cells

To measure cell growth, cells were seeded at $10^4$ cells/cm$^2$ on 6-well plates (Corning Co.) pre-coated with collagen and cultured for 24 h. The medium was changed to fresh medium containing 5% FCS and growth factors were added. The medium was changed every third days and growth factors were added in each time. The numbers of the cells were counted using a hematocytometer following dissociation of the cells by trypsin treatment. Data are averaged of triplicate measurements.

To determine survival of PC12 cell, cells were plated at $5 \times 10^4$ cells/cm$^2$ on 6-well plates and cultured for 24 h. The medium was changed to fresh medium containing 1% FCS.

For measurement of DNA synthesis, PC12 cells were plated at a density of $10^5$ cells/well on a collagen coated 24-well plate (Costar Co.). The next day, the medium was changed to fresh medium containing lower concentration of FCS (2.5%) and cultured for 24 h. Growth factors were added and the cells were cultured for 24 h followed by labeling with 1 µCi of $^{125}$I-deoxyuridine (2200 Ci/mmol, New England Nuclear) for 12 h. Cultures were washed once with PBS and once with 10% (w/v) ice cold TCA. Cells were solubilized with 1 M NaOH and radioactivity incorporated into nuclei was counted in a γ-counter.

(8) Protein Assay

Protein concentration was measured by micro BCA protein assay system (Pierce Chemical Co.) using bovine serum albumin as the standard.

(9) Primary Culture of Hippocampal Neurons

Hippocampani were dissected from embryonic day 18 rats and incubated for 8 min at 37° C. in 0.25% trypsin. The solution was removed and residual trypsin was inactivated with appropriate amount of FCS or horse serum (HS). The cells were dissociated by trituration through plastic tips. The dissociated neurons were plated into 48-well plates (Costar Co.) precoated with polyethyleneimine (Sigma Co.) at a density of $10^5$ cells/cm$^2$. The neurons were grown in a mixture of Dulbecco's modified Eagle's (DME) medium and Ham's F12 medium (1:1) supplemented with 5% FCS and 5% HS in a 90% air/10% $CO_2$ humidified incubator (37° C.). The culture medium was replaced with DME containing 10% Nu-Serum (Collaborative Research Co.) in place of the FCS or HS at 12–24 h after seeding.

(10) Experimental Cerebral Ischemia 9 weeks-old male wistar rats were used for the operation. Cerebral ischemia was induced by insertion of embolus into the right internal carotid artery to stop the blood flow into the middle cerebral artery. The embolus was inserted for 2 h and then blood flow was recirculated. Following appropriate period after recirculation, animals were killed and right and left-brains were removed separately.

EXAMPLE 1
Changes in HGF mRNA and c-met mRNA levels in Rat Brain

Changes in HGF mRNA and HGF receptor levels in brain during rat development were examined by Northern blot analysis mentioned before.

Namely, total RNA (50 µg/lane) was electrophoresed in a 1.0% agarose/formaldehyde gel and transferred to a Biodyne-β filter. The membrane was hybridized with a $^{32}$P-labeled rat HGF cDNA and rat c-met cDNA probe as described in Materials and Methods. The results are shown in FIG. 1. In FIG. 1, the lower photographs show the signals of the glutaraldehyde 3-phosphate dehydrogenase (GAPDH) as internal controls.

FIG. 1 shows changes in HGF mRNA and c-met mRNA expression in rat brain during late-fetal, neonatal and adult stages. HGF mRNA was detected at very low level in the brain at late-fetal stage, while it increased after birth and reached a maximum at adult stage. On the other hand, c-met mRNA level was expressed in late-fetal brain and it increased markedly after birth, reaching a maximum at day 5. However, c-met mRNA level was remarkably decreased until adult stage. This result that HGF and its receptor mRNAs are continuously expressed in brain from late-fetal to adult stages suggested that HGF may have some roles in brain.

To investigate possible role of HGF in brain, then regional expressions of HGF mRNA and c-met mRNA in brain were examined and effects of HGF on neural cells in vitro were analyzed by the methods mentioned below.

EXAMPLE 2
Regional Expressions of HGF mRNA and c-met mRNA in Adult Rat Brain Regional expressions of HGF mRNA and c-met mRNA in adult rat brain were examined by Northern blot analysis mentioned before.

Figure 2:
FIG. 2 is a photograph of Northern blot analysis when RNA was electrophoresed in agarose/formaldehyde gel, showing regional expressions of HGF mRNA and c-met mRNA in adult rat brain.
Figure 2:
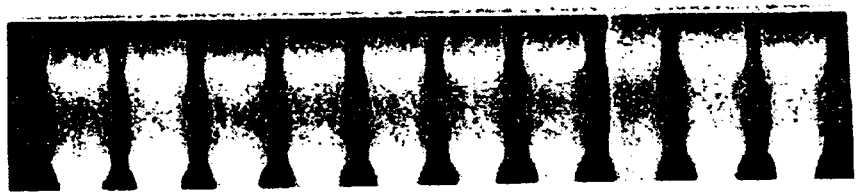

Namely, 30 µg or 50 µg per lane of total RNA was electrophoresed, respectively, and transferred to a Biodyne-β filters. The membrane was hybridized with $^{32}$P-labeled rat HGF cDNA and rat c-met cDNA probes as described in Materials and Methods. The results are shown in FIG. 2. In FIG. 2, the lowerest photograph shows the signals of the 18S and 28S rRNA, visualized by ethidium bromide staining.

FIG. 2 shows the expression of HGF mRNA and c-met mRNA in various regions of adult rat brain. HGF mRNA was detected in various regions in brain and it was expressed at relatively high level in hippocampus, olfactory bulb, cortex, and cerebellum. The c-met mRNA was also expressed in various regions in brain and was expressed at relatively high level in hippocampus and olfactory bulb.

EXAMPLE 3
Effects on Growth and Survival of PC12 Cells

To examine the functions of HGF in brain, PC12 cell culture system was used.

① First, to examine the effect of HGF on proliferation of PC12 cells. PC12 cells were cultured in medium containing 5% FCS in the presence or absence of HGF. Namely, PC12 cells were plated on collagen-coated 6-well plates at a density of $10^5$ cells/well. The next day, medium was changed to fresh medium containing 5% FCS and the cells were cultured for given days in the absence (○) or presence of 1 ng/ml (●), 3 ng/ml (△) or 10 ng/ml HGF (▲), and the numbers of cells were counted (see Materials and Methods). The results are shown in FIG. 3A. Each value represents mean of triplicate measurements and standard deviations were below 0.3% of each value.

As shown in FIG. 3A, the stimulatory effect of HGF on proliferation of PC12 cells was seen from day 4 to day 10 in culture, and HGF increased the number of the cells in a dose-dependent manner: 1.1. 1.3 and 1.4-fold increase were seen by 1, 3, 10 ng/ml HGF, respectively.

② Since the proliferation of PC12 cells is known to be ceased by NGF, but enhanced by EGF, effects of HGF, EGF, NGF and their combinations on the growth of PC12 cells were compared. PC12 cells were cultured as described in above ①, and growth factors were used as following concentrations: HGF 10 ng/ml; EGF 10 ng/ml; NGF 20 ng/ml. Cell number was determined on 8th day after plating of the cells. The results are shown in FIG. 3B. Each value represents mean of triplicate measurements and standard deviations were below 0.3% of each value.

As shown in FIG. 3B, the number of the cells was increased 1.4-fold by the addition of 10 ng/ml HGF while 2.1-fold increase was seen by the addition of 10 ng/ml EGF. The combination of 10 ng/ml HGF and 10 ng/ml EGF resulted in 2.4-fold increase in cell number compared to that seen in the absence of growth factors. Thus, HGF and EGF additively stimulated the proliferation of PC12 cells. On the other hand, the proliferation of PC12 cells was not affected by 20 ng/ml NGF. Moreover, the number of PC12 cells was not increased by HGF when simultaneously added with NGF.

③ To examine whether HGF induces mitogenesis in PC12 cells, the effect of HGF on DNA synthesis was examined. Namely, PC12 cells were plated at a density of $10^5$ cells/well on a collagen-coated 24-well plate. Uptake of $^{125}$I-deoxyuridine were measured as described in Materials and Methods. The results are shown in Table 1. Each value represents mean of triplicate measurements and standard deviations.

As shown in Table 1, neither HGF nor EGF did significantly stimulate DNA synthesis of PC12 cells, whereas NGF inhibited DNA synthesis dose-dependently.

TABLE 1

| Growth | $^{125}$I-deoxyuridine uptake (cpm/μg protein) | | | | |
|---|---|---|---|---|---|
| factor | 0 ng/ml | 1 ng/ml | 5 ng/ml | 10 ng/ml | 20 ng/ml |
| None | 380 ± 1.8 | — | — | — | — |
| HGF | — | 366 ± 6.9 | 367 ± 4.3 | 382 ± 9.7 | 352 ± 2.1 |
| EGF | — | 395 ± 10.1 | 380 ± 6.5 | 387 ± 10.5 | 369 ± 8.9 |
| NGF | — | 380 ± 1.8 | 277 ± 3.1 | 259 ± 6.3 | 218 ± 10.0 |
| 5% FCS | 492 ± 7.1 | — | — | — | — |

④ Since HGF did not enhance the proliferation of PC12 cells as mentioned above, the effect of HGF on survival of PC12 cells cultured in the medium containing 1% FCS was examined, in order to examine whether HGF prolongs survival of PC12 cells.

Namely, PC12 cells were plated on collagen coated 6-well plates at a density of 5×10⁵ cells/well. The next day, the medium was changed to fresh medium containing 1% FCS and cultured in the presence of HGF at concentrations of 1 ng/ml (●), 3 ng/ml (Δ), 10 ng/ml (▲) and in the absence of HGF. The results are shown in FIG. 4. Each value represents mean of triplicate measurement and standard deviations were below 0.6% of each value.

As shown in FIG. 4, in the absence of HGF, about 40% of the total cells died from culture dishes during 4 days of culture period and most of the cells died until day 10 in culture. In contrast to it, the decrease in cell number was not observed in the presence of HGF. The initial number of PC12 cells was maintained at least during 13 days of culture period in the presence of HGF and 1 ng/ml HGF was fully effective on survival of PC12 cells in this condition.

⑤ Effects of HGF, EGF and NGF on differentiation of PC12 cells were examined. Namely. PC12 cells were cultured in the medium containing 12% FCS in the absence (A) or presence of 10 ng/ml HGF (B), 10 ng/ml EGF (C), 20 ng/ml NGF (D), 10 ng/ml HGF plus 10 ng/ml EGF (E), 10 ng/ml HGF plus 20 ng/ml NGF (F). Cells were cultured for 7 days in each conditions, and morphological changes of cells were observed. The results are shown in FIG. 5.

Figure 5A:
FIG. 5 is a photomicrograph showing morphological changes of PC12 cells cultivated in the presence or absence of HGF, EGF or NGF.
Figure 5B:
Figure 5C:
Figure 5D:
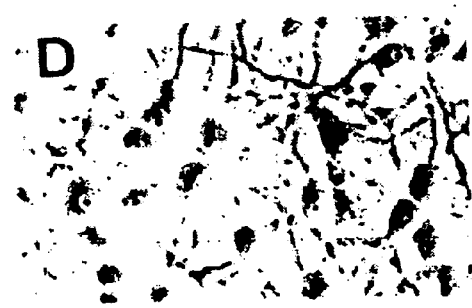
Figure 5E:
Figure 5F:
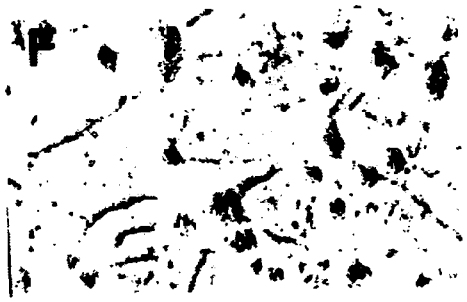

As shown in FIG. 5, although PC12 cells showed a round-shaped appearance, addition of NGF induced differentiation of PC12 cells into a sympathetic neuronal phenotype as evidenced by neurite outgrowth (FIGS. 5A and D). However, there was no morphological change after addition of HGF and HGF-treated cells were indistinguishable from untreated cells (FIG. 5B). Since neither EGF nor combination of HGF and EGF induced neurite outgrowth (FIGS. 5C and E), these growth factors do not induce differentiation of PC12 cells. The simultaneous addition of HGF and NGF resulted in induction of differentiated morphology of PC12 cells, suggesting that intracellular signals triggered by NGF largely overcome those triggered by HGF.

⑤ HGF receptor analyses on PC12 cells and other neuronal cell lines were carried out. Namely, binding of $^{125}$I-HGF to PC12 cells cultured in the absence or presence of NGF was measured. The binding of $^{125}$I-HGF to PC12 cells was determined as described in Materials and Methods. The results are shown in FIG. 6. In FIG. 6, (A) represents saturation curves of specific binding of $^{125}$I-HGF to PC12 cells cultured in the absence (●) or presence of 50 ng/ml NGF (○). (B) represents scatchard plot of the binding of $^{125}$I-HGF to PC12 cells.

As shown in FIG. 6A, $^{125}$I-HGF specifically bound to the undifferentiated PC12 cells cultured in the absence of NGF. Scatchard analysis of the binding indicates that exponentially growing PC12 cells express binding sites of 185 sites/cell with a Kd value of 40 pM (FIG. 6B). When PC12 cells were differentiated into neuronal phenotype during 7 days' culture in the presence of 50 ng/ml NGF, specific binding of $^{125}$I-HGF was remarkably reduced (FIG. 6A). Scatchard analysis revealed that these PC12 cells express binding sites of 15 sites/cell with a Kd value of 27 pM (FIG. 6B) Thus, the binding sites of HGF were reduced from 185 sites/cell to 15 sites/cell during the differentiation of PC12 cells.

Binding of 125I-HGF to other cell lines derived from central nervous system was also measured. The results are shown in Table 2. As shown in Table 2, high affinity HGF receptor was also found in human glioblastoma T98G, human neuroblastoma GOTO and SCCH-26, which express binding sites of 540, 120, 60 sites/cell, respectively, with Kd values of 30–40 pM.

TABLE 2

| Cell | Origin | Kd (pM) | B max (sites/cell) |
|---|---|---|---|
| T98G | Human, glioblastoma | 31 | 540 |
| PC12 | Rat, pheochromocytoma | 40 | 185 |
| GOTO | Human, neuroblastoma | 30 | 120 |
| SCCH-26 | Human, neuroblastoma | 20 | 60 |

EXAMPLE 4

Effect on Hippocampal Neurons in Primary Culture

Figure 7:
FIG. 7 is a photomicrograph showing the morphology of hippocampal nerve cell, showing that HGF prolongs survival of hippocampal nerve cell in primary culture.
Figure 7:
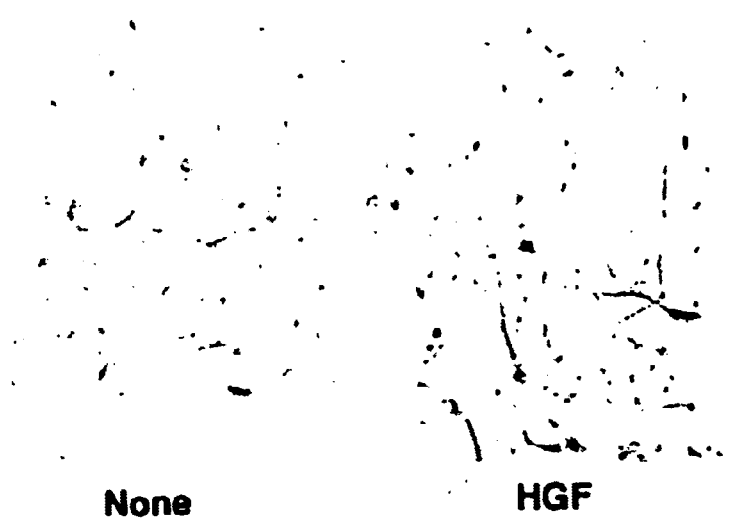

Since it turned out that HGF acts as a survival factor for PC12 cells, tests determining whether HGF has ability to prolong survival of nerve cells in primary cultur were examined. Hippocampal neurons were primarily cultured in the presence or absence of HGF, and morphological appearances of the cells at day 1 and day 6 in culture were measured. The results are shown in FIG. 7. As shown in FIG. 7, when hippocampal neurons cultured in the absence of HGF for 6 days, most of the cells died. The addition of HGF to these cultures resulted in increased number of survived neurons. Thus HGF acts as a survival factor for hippocampal neurons in primary culture.

EXAMPLE 5

Induction of HGF mRNA and c-met mRNA in Brain After Cerebral Ischemia

Figure 8:
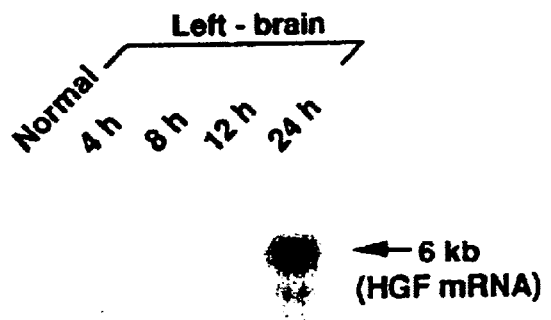
FIG. 8 is a photograph of Northern blot analysis when RNA was electrophoresed in agarose/formaldehyde gel, showing induction of HGF mRNA and c-met mRNA expression in brain after experimental cerebral ischemia.
Figure 8:
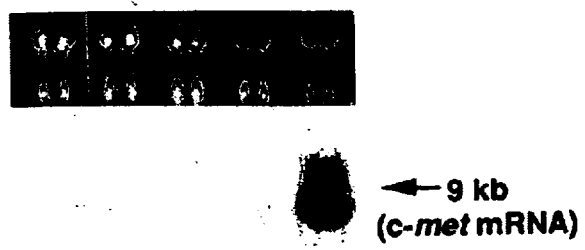

Since it is clarified that HGF acts as a survival factor for neurons in primary culture, the protective effect of HGF on neuronal degeneration following cerebral injuries was examined in the experimental cerebral ischemia. The experimental cerebral ischemia was carried out as described in Materials and Methods. Total RNA was extracted from right and left-brain at 4, 8, 12 and 24 h after recirculation, and HGF mRNA and c-met mRNA levels were measured by Northern blot analysis as described in Materials and Methods. The results are shown in FIG. 8. In FIG. 8, the lower photographs show the signals of the 18S and 28S rRNA, visualized by ethidium bromide staining.

In this experimental condition, major ischemic lesions were induced in right-brain, while left-brain was also injured after blood recirculation slightly in retard of right-brain. In right-brain, HGF mRNA was induced from 12 h after recirculation and remarkable induction was seen after 24 h. In left-brain, HGF mRNA increased markedly 24 h after recirculation.

On the other hand, c-met mRNA was markedly induced in the similar time-dependency with that of HGF mRNA. In right-brain, c-met mRNA increased from 12 h after recirculation and remarkable increase was seen 24 h after ischemic treatment. In left-brain c-met mRNA was induced 12 h after treatment and was markedly increased after 24 h.

On the other hand, only a little induction of both HGF and c-met mRNAs was observed in sham-operated animals.

PREPARATION EXAMPLE 1

A solution containing 1 mg of HGF, 1 g of mannitol and 10 mg of polysorbate 80 in 100 ml of physiological saline was aseptically prepared. 1 ml of the solution was poured into each vial and lyophilized, and then the vial was sealed to obtain a freeze-dried preparation.

PREPARATION EXAMPLE 2

A solution containing 1 mg of HGF and 100 mg of human serum albumin in 100 ml of 0.02M phosphate buffer (containing 0.15M of NaCl and 0.01% of polysorbate 80, pH 7.4) was aseptically prepared. 1 ml of the solution was poured into each vial and lyophilized, and then the vial was sealed to obtain a freeze-dried preparation.

PREPARATION EXAMPLE 3

A solution containing 1 mg of HGF, 2 g of sorbitol, 2 g of glycine and 10 mg of polysorbate 80 in 100 ml of distilled water for injection was aseptically prepared. 1 ml of the solution was poured into each vial and lyophilized, and then the vial was sealed to obtain a freeze-dried preparation.

What is claimed is:

1. A method of promoting survival of neurons following cerebral stroke/ischemia or promoting survival of hippocampal or olfactory bulb neurons of a human or a mammal, which comprises administering an effective amount of human HGF protein comprising SEQ ID NO: 2 or SEQ ID NO:4.

2. A method of prolonging the survival of neurons following cerebral stroke/ischemia or prolonging the survival of hippocampal or olfactory bulb neurons comprising contacting the neurons with an effective amount of human HGF protein comprising SEQ ID NO: 2 or SEQ ID NO:4.

3. A method of prolonging survival of hippocampal or olfactory bulb neurons during cerebral stroke and cerebral infarction, which comprises administering an effective amount of human HGF protein comprising SEQ ID NO: 2 or SEQ ID NO: 4.

* * * * *